United States Patent [19]

Zhukov et al.

[11] Patent Number: 5,037,997
[45] Date of Patent: Aug. 6, 1991

[54] METHOD OF PREPARING 1-BUTENE AND/OR HEXENES

[75] Inventors: Viktor I. Zhukov, Grozny; Gennady P. Belov, Moskovskaya; Galina S. Sergienko, Grozny; Zinaida M. Dzhabieva, Moskovskaya; Saida R. Ivolgina, Grozny; Natalya V. Kartasheva, Stavropolsky krai; Fridrikh S. Dyachkovsky, Moscow; Sergei S. Ivanchev, Leningrad; Vladimir L. Proskurnin, Grozny; Jury M. Petrov; Olga N. Reznikova, both of Stavropolsky krai, all of U.S.S.R.

[73] Assignees: Institut Khimicheskoi Fiziki an SSSR; Groznensky Filial Oppo; Po Stavropolpolimer, all of Budenovsk, U.S.S.R.

[21] Appl. No.: 445,869
[22] PCT Filed: Feb. 23, 1988
[86] PCT No.: PCT/SU88/00042
  § 371 Date: Dec. 18, 1989
  § 102(e) Date: Dec. 18, 1989
[87] PCT Pub. No.: WO89/08091
  PCT Pub. Date: Sep. 8, 1989
[51] Int. Cl.$^5$ ............................................. C07C 2/24
[52] U.S. Cl. ..................................... 585/512; 502/115
[58] Field of Search ......................... 585/512; 502/115

[56] References Cited

U.S. PATENT DOCUMENTS

| | | | |
|---|---|---|---|
| 2,943,125 | 6/1960 | Ziegler et al. | 585/512 |
| 3,911,042 | 10/1975 | Belov et al. | 585/512 |
| 3,969,429 | 7/1976 | Belov et al. | 585/512 |
| 4,615,998 | 10/1986 | Le Quan et al. | 585/512 |
| 4,771,023 | 9/1988 | Sasaki et al. | 502/115 |
| 4,898,847 | 2/1990 | Salajka et al. | 502/115 |
| 4,916,099 | 4/1990 | Sasaki et al. | 502/115 |
| 4,942,148 | 7/1990 | Furuhashi et al. | 502/115 |

Primary Examiner—H. M. S. Sneed
Assistant Examiner—James Saba
Attorney, Agent, or Firm—Burgess, Ryan & Wayne

[57] ABSTRACT

A method of preparing 1-butene and/or hexenes resides in dimerization of ethylene and/or co-dimerization of ethylene and propylene in an organic solvent under an increased pressure and at a temperature of 0° to 100° C. in the presence of a complex organometallic catalyst. The catalyst contains titanium alcoholate of the formula Ti(OR$^1$)$_4$, where R$^1$ is an alkyl radical having from 1 to 8 carbon atoms or aryl, trialkylaluminium of the formula AlR$^2$$_3$, where R$^2$ is an alkyl radical having from 1 to 6 carbon atoms, an organomagnesium compound of the formula MgR$^2$$_2$ and/or MgR$^3$X, where R$^3$ is an alkyl radical having from 1 to 4 carbon atoms and X is Br, Cl, or I.

3 Claims, No Drawings

METHOD OF PREPARING 1-BUTENE AND/OR HEXENES

FIELD OF THE INVENTION

The present invention relates to petroleum chemistry and more particularly to a method of preparing butene-1 and/or hexenes.

BACKGROUND OF THE INVENTION

Known in the art is a method of preparing 1-butene or hexenes (SU, A, 65B119) by dimerization of ethylene or co-dimerization of etylene and propylene in the presence of the catalyst consisting of titanium alcoholate of the formula $Ti(OR)_4$ and a complex organoaluminium compound of the formula $AlR_3L$, where L is an alkyl radical having from 1 to 4 carbon atoms and L is a compound selected from the group dialkyl ether, dialkylamine, aliphatic diamine, di(diphenylphosphino) ethylamine, and diethylsulphide. The interaction of monomers is performed in an organic solvent at a temperature of 0°–80° C. under pressure 0.1–20.0 MPa. The known method is characterized by a low yield of the final product (up to 390 g/g $Ti(OR)_4$) and by the formation of a solid polymer (up to 0.1 mass %) in the reaction zone. Also known in the art is a method of preparing 1-butene (SU, A, 459451) residing in dimerization of ethylene in the presence of a complex organometallic catalyst consisting of tetraalkoxytitanate, trialkylaluminium (Alk=$C_1$–$C_4$) and an organic additive: isopropanol, butanol, or phenol, in an organic solvent at a temperature of from 70° to 80° C. under pressure from 0.25 to 1.4 MPa. The process is highly selective (99.75 vol. % of 1-butene) but the yield of 1-butene is low (101–214 g/g $Ti(OR)_1$ per hour).

Likewise known in the art is a method of preparing 1-butene and/or hexenes U.S. Pat. No. 4,101,600) residing in dimerization of ethylene and/or co-dimerization of ethylene and propylene in the presence of a complex organometallic catalyst containing titanium alcoholate of the formula $Ti(OR^1)_4$, where $R^1$ is an alkyl radical having from 1 to 8 carbon atoms or aryl, trialkylaluminium of the formula $AlR^2_3$, where $R^2$ is an alkyl radical having from 1 to 6 carbon atoms, at a temperature of from 0° to 100° C. under enhanced pressure in an organic solvent. To increase the activity and selectivity of the catalyst, it is pre-treated with an ethylene-hydrogen mixture. The mixture is, however, dangerously explosive which complicates the technological process and requires a special equipment. The yield of 1-butene is low and amounts only to 80–347 g/g $Ti(OR^1)_4$ per hour, although the content of hexenes in the firnal product attains 25 mass % in the presence of solid polymer in amount to 0.4 mass %.

DISCLOSURE OF THE INVENTION

The main object of the invention is to develop a method of preparing 1-butene and/or hexenes by a quantitative change of a complex organometallic catalyst which will provide an increase in the yield of the final product without a complication of technology.

Said object is accomplished by the provision of a method of preparing 1-butene and/or hexenes, residing in dimerization of ethylene and/or co-dimerization of ethylene and propylene in the presence of a complex organometallic catalyst containing titanium alcoholate of the formula $Ti(OR^1)_4$, where $R^1$ is an alkyl radical having from 1 to 8 carbon atoms or aryl, trialkylaluminium of the formula $AlR^2_3$, where $R^2$ is an alkyl having from 1 to 6 carbon atoms, at a temperature of from 0° to 100° C. and under increased pressure in an organic solvent, according to the invention, use is made of a complex organometallic catalyst containing additionally an organomagnesium compound of the formula $MgR^3_2$ and/or $MgR^3X$, where $R^3$ is an alkyl radical having from 1 to 4 carbon atoms and X is Br, Cl, or I. The use of such a catalyst enhances the yield of the final product to 1300 g/g $Ti(OR^1)_4$ and decreases the yield of side products (octenes and solid polymer) 2–100 times.

To perform the process under optimum conditions and with a maximum yield of the final product, it is expedient to use the above catalyst containing $Ti(OR^1)_4$, $AlR^2_3$, $MgR^3_2$, and/or MgRX at a mole ratio of 1.0:1.0–100:0.2–5.0, respectively.

To simplify the technological process, it is recommended to use as a hydrocarbon organic solvent 1-butene and/or hexene fraction.

DETAILED DESCRIPTION OF THE INVENTION

An organic solvent containing $Ti(OR^1)_4$, $AlR^2_3$, and $MgR^3_2$ and/or $MgR^3X$ is introduced into a reactor at a mole ratio 1.0:1.0–100:0.2–0.5, respectively, wherein ethylene and/or a mixture of ethylene and propylene is also fed and dimerization or co-dimerization is carried out at a temperature of from 0° to 100° C. under pressure from 0.1 to 4 MPa up to the formation of 1-butene and/or a hexene fraction containing (vol. %) 3-methyl-1-pentene, 1-hexene, and 2-ethyl-1-butene.

As an organic solvent use can be made of aliphatic (propane, butene, heptane, hexane, octane), aromatic (benzene, toluene), or heteroatom-containing (alkyl halide, ethers, and esters) hydrocarbon solvent. A maximum simplification of the technological process is attained when 1-butene or a hexene fraction is used as an organic solvent. The solvent recuperation stage is ruled out completely and the yield of the final product is greatly increased.

In the presence of olefin $Ti(OR^1)_4$, $AlR^2_3$, $MgR^3_2$ and/or $MgR^3X$ form in an organic solvent a complex organometallic catalyst. Said organometallic compound can be introduced into the reaction zone simultaneously with $Ti(OR^1)_4$ and $AlR^2_3$ or after the delivery of olefin. The use of an organomagnesium compound as the third component of the complex catalyst, according to the invention, enhances considerably the activity of the catalyst. This, in its turn, ensures a rise in the rates of dimerization and co-dimerization and an increase in selectivity of these processes.

The process is greatly intensified and the yield of the final product attains 1300 g/g $Ti(OR^1)_4$ per hour or 9.2 kg/g Ti.

The specific examples of realizing the present invention are given hereinbelow by way of illustration.

EXAMPLE 1

Heptane (150 ml), $Ti(OC_4H_9)_4$ ($0.256 \times 10^{-3}$ mole), $Al(C_2H_5)_3$ ($0.96 \times 10^{-3}$ mole), and $MgC_4H_9Cl$ ($0.128 \times 10^{-3}$ mole) at a mole ratio of 1.0:4.0:0.5, respectively, are fed into a reactor and then ethylene is delivered. Dimerization is carried out at a temperature of 40° C. under ethylene pressure 0.7 MPa. The yield of the product is 440 g/g $Ti(OC_4H_9)_4$ per hour or 3.1 kg/g Ti per hour. The final product has the following composition (vol. %): 1-butene 95.4; 1-hexene 0.1; 3-methyl-1-pentene 1.4; 2-ethyl-1-butene 1.B; polymer - traces.

EXAMPLE 2

The process of ethylene dimerization is performed as described in Example 1 at a mole ratio $Ti(OC_4H_9)_4$: $Al(C_2N_5)_3:MgC_4H_9Cl = 1.0:4.18:2.0$. The yield of the product is 632 g/g $Ti(OC_4H_9)_4$ per hour or 4.8 kg/g Ti per hour. The product has the following composition (vol. %): 1-butene 96.9; 1-hexene 0.2; 3-methyl-1-pentene 1.1; 2-ethyl-1-butene 1.3; polymer - traces.

EXAMPLE 3

The process of ethylene dimerization is performed by following the procedure described in Example 1 at a mole ratio $Ti(OC_4H_9)_4:Al(C_2H_5)_3:MgC_4H_9Cl = 1.0:4.7:5.0$.

The yield of the product is 740 g/g $Ti(OC_4H_9)$ per hour or 5.2 kg/Ti g per hour. The product has the following composition (vol. %): 1-butene 97.6; 1-hexene 0.3; 3-methyl-1-pentene 0.B; 2-ethyl-1-butene 1.3; polymer traces.

EXAMPLE 4

Dimerization of ethylene is carried out at 65° C. as described in Example 1. As MgRX use is made of $MgC_2H_5Br$. Mole ratio $Ti(OC_4H_9)_4:Al(C_2H_5)_3:MgC_2H_5Br = 1.0:3.72:1.0$.

The yield of the product is 503 g/g $Ti(OC_4H_9)_4$ per hour or 3.6 kg/g Ti per hour. The product has the following composition (vol. %): 1-butene 96.9; 1-hexene 0.4; 3-methyl-1-pentene 1.1; 2-ethyl-1-butene 1.6; polymer traces.

EXAMPLE 5

Dimerization of ethylene is performed as described in Example 1 but use is made of $MgCH_3I$ and a mole ratio $Ti(OC_4H_9)_4:Al(C_2H_5):MgCH_3I$ is 1.0:4.0:0.5.

The yield of the product is 273 g/g $Ti(OC_4H_9)_4$ per hour of 1.9 kg/g Ti per hour. The product has the following composition (vol. %): 1-butene 97.B; 1-hexene 0.2; 3-methyl-1-pentene 0.5; 2-ethyl-1-butene 0.6; polymer traces.

EXAMPLE 6

A hexane fraction (150 ml), $Ti(OC_4H_9)_4$ ($0.256 \times 10^{-3}$ mole), $Al(C_2H_5)_3$ ($0.752 \times 10^{-23}$ mole), and $MgC_2H_5Br$ ($0.128 \times 10^{-23}$ mole) are supplied to a reactor at mole ratio of 1.0:2.94:0.5, respectively, and then ethylene is delivered. Dimerization is carried out at 40° C. under ethylene pressure 0.7 MPa. The yield of 1-butene is 98 g/g $Ti(OC_4H_9)_4$ per hour or 0.695 kg/g Ti per hour; the selectivity of the process in 1-butene is 82 vol. %.

EXAMPLE 7

Dimerization of ethylene is performed by following the procedure described in Example 6 at a mole ratio $Ti(OC_4H_9)_4:Al(iso-C_4H_9)_3:MgC_2H_5Br = 1.0:2.9:2.0$. The yield of 1-butene is 95 g/g $Ti(OC_4H_9)_4$ per hour or 0.674 kg/g Ti per hour, the selectivity of the process in 1-butene is 87.4 vol. %.

EXAMPLE 8

Dimerization of ethylene is performed by following the procedure described in Example 6 at a mole ratio $Ti(OC_4H_9)_4:Al(iso-C_4H_9)_3:MgC_2H_5Br = 1.0:4.0:4.0$. The yield of 1-butene is 90 g/g $Ti(OC_4H_9)_4$ per hour or 0.639 kg/g Ti per hour° The selectivity of the process in 1-butene is 88.1 vol. %.

EXAMPLE 9

Dimerization of ethylene is carried out by following the procedure described in Example 1 but as $MgR_2$ use is made of $Mg(C_2H_5)_2$. Mole ratio $Ti(OC_4H_9)_4:Al(C_2H_5)_3:Mg(C_2H_5)_2 = 1.0:3.72:1.0$. The yield of the product is 490 g/g $Ti(OC_4H_9)_4$ per hour or 3.5 kg/g Ti per hour. The product has the following composition (vol. %): 1-butene 96.1; 1-hexene 0.4; 3-methyl-1-pentene 1.6; 2-ethyl-1-butene 1.9; polymer - traces.

EXAMPLE 10

Dimerization of ethylene is carried out by following the procedure described in Example 1 but as $MgR_2$ use is made of $Mg(C_4H_9)_2$. Mole ratio $Ti(OC_4H_9)_4: Al(C_2H_5)_3:Mg(C_4H_9)_2 = 1.0:3.72:1.0$. The yield of the product is 445 g/g $Ti(OC_4H_9)$ per hour or 3.1 kg/g Ti per hour. The product has the following composition (vol. %): 1-butene 96.0; 1-hexene 0.1; 3-methyl-1-pentene 1.6; 2-ethyl-1-butene 2.3; polymer - traces.

EXAMPLE 11 n-Heptane (200 ml), $Al(C_2H_5)_3$ ($2.2 \times 10^{-3}$ mole), and $Ti(OC_6H_5)_4$ ($1.45 \times 10^{-3}$ mole) are delivered to a reactor and then an ethylene-propylene mixture is fed at a mole ratio 1:1. After that $MgC_2H_5Br$ ($2.9 \times 10^{-3}$ mole) are introduced. Mole ratio $Ti(OC_6H_5)_4:Al(C_2H_5)_3:MgC_2H_5Br = = 1.0:3.4:2.0$. Dimerization is performed at 30° C. under pressure 0.1 MPa for 60 min and terminated by the addition of alcohol. The yield of the product is 2.3 g or 191 g/g Ti per hour. The product has the following composition (vol. %) 1-butene 60.7; 3-methyl-1-butene 9.3; 2-methyl-1-butene 21.B; 3-methyl-1-pentene 5.4; 2-ethyl-1-butene 2.8.

EXAMPLE 12

Co-dimerization of ethylene and propylene is performed by following the procedure described in Example 11 but as $Ti(OR_4)$ use is made of $Ti(OC_4H_9)_4$. Mole ratio $Ti(OC_4H_9)_4:Al(C_2H_5)_3:Mg(C_2H_5Br) = 1.0:3.4:2.0$. The yield of the product is 3.5 g or 24B g/g Ti per hour. The final product has the following composition (vol. %) 1-butene 55.3; 3-methyl-1-butene 15; 2-methyl-1-butene 19; 3-methyl-1-pentene 7.4; 2-ethyl-1-butene 3.6; polymer - traces

EXAMPLE 13

Dimerization of ethylene is performed at 80° C. by following the procedure described in Example 1 at a mole ratio $Ti(OC_4H_9)_4:Al(iso-C_4H_9)_3:MgC_2H_5Br = 1.0:2.0:0.3$. The yield of 1-butene is 90 g/g $Ti(OC_4H_9)_4$ per hour or 539 g/g Ti per hour. The selectivity of the process in 1-butene is 69 vol. %.

EXAMPLE 14

Dimerization of ethylene is performed in 1-butene at 65° C. under ethylene pressure 1.4 MPa. The catalyst is used as in Example 1 at a mole ratio $Ti(OC_4H_9)_4::Al(C_2H_5)_3:MgC_4H_9Cl = 1.0:4.7:5.0$. The yield of the product is 495 g/g $Ti(OC_4H_9)_4$ per hour or 3.5 kg/g Ti per hour. The product has following composition (vol. %): 1-butene 95.B; 3-methyl-1-pentene 1.8; 1-hexene 0.2%; 2-ethyl-1-butene 2.1; olefin fraction $C_6-C_{12}$ 0.05; polymer 0.05.

EXAMPLE 15

Dimerization of ethylene is performed in a hexene fraction containing (vol. %): 3-methylene-1-pentene 33; 2-ethyl-1-butene 55; 1-hexene 12; at 35° C. under pressure 1.4 MPa. The catalyst is used as described in Examples 1 and 14.

The yield of the product is 460 g/g Ti(OC$_4$H$_9$)$_4$ per hour or 3.2 kg/g Ti per hour. The product has the following composition (vol. %): 1-butene 94.5; hexenes 5.42; octenes and polymer 0.08.

EXAMPLE 16 n-Heptane (200 ml) containing Ti(OC$_4$H$_9$)$_4$ (1.6×10$^{-3}$ mole), Al(C$_2$H$_5$)$_3$ (6.4×10$^{-3}$ mole), and a mixture (1.6××10$^{-3}$ mole) of MgC$_4$H$_9$Cl and Mg(C$_4$H$_9$)$_2$(3:1) are fed into a reactor and then ethylene is supplied. Mole ratio Ti(OC$_4$H$_9$)$_4$:Al(C$_2$H$_5$)$_3$: mixture of MgC$_4$H$_9$Cl and Mg(C$_4$H$_9$)$_2$==1.0:3.84:1.0. Dimerization is carried out at 55° C. under pressure of 0.8 MPa. The yield of the product is 872 g/g Ti(OC$_4$H$_9$)$_4$ per hour or 6.2 kg/g Ti per hour. The product has the following composition (vol. %):1-butene 99.4; 3-methyl-1-pentene 0.2; 1-hexene 0 1; 2-ethyl1-butene 0.3.

EXAMPLE 17

Dimerization of ethylene is carried out at 30° C. by following the procedure described on Example 16 but as MgRX use is made of MgCH$_3$I. Mole ratio Ti (OC$_4$H$_9$)$_4$: :Al(C$_2$H$_5$)$_3$:MgCH$_3$I=1.0:4.0:0.2. The yield of the product is 469 g/g Ti(OC$_4$H$_9$)$_4$ per hour or 3.3 kg/g Ti per hour.

The product has the following composition (vol. %): 1-butene 96.7; 3-methyl-1-butene 1.5; 1-hexene 0.2; 2-ethyl-1-butene 1.6; polymer 0.01.

EXAMPLE 18

Ethylene dimerization is carried out at 65° C. as described in Example 16 but as MgR$_2$ use is made of Mg(C$_4$H$_9$)$_2$. Mole ratio Ti(OC$_4$H$_9$)$_4$:Al(C$_2$H$_5$)$_3$:Mg(C$_4$H$_9$)$_2$==1.0:9.2:0.50. The yield of the product is 767 g/g Ti(OC$_4$H$_9$)$_4$ per hour or 5.4 kg/g Ti per hour. The product has the following composition (vol. %): 1-butene 94.9; 3-methyl-1-butene 2.1; 1-hexene 0.3; 2-ethyl-1-butene 2.7; polymer 0.2.

EXAMPLE 19

Dimerization of ethylene is performed at 80° C. by following the procedure described in Example 16 but as MgR$_2$ use is made of Mg(C$_4$H$_9$)$_2$. Mole ratio Ti(OC$_4$H$_9$)$_4$: Al(C$_2$H$_5$)$_3$:Mg(C$_4$H$_9$)$_2$=1.0:7.65:2.0. The yield of the product is 750 g/g Ti(OC$_4$H$_9$)$_4$ per hour or 5.3 kg/g Ti per hour.

The product has the composition (vol. %): 1-butene 94.2; 3-methyl-1-butene 2.2; 1-hexene 0.5; 2-ethyl-1-butene 3.1.

EXAMPLE 20

Dimerization of ethylene is carried out at 25° C. by following the procedure described in Example 16 but as MgRX use is made of a mixture of MgC$_2$H$_5$Br and Mg(C$_2$H$_5$)$_2$ (4:1). Mole ratio Ti(OC$_4$H$_9$)$_4$:Al(C$_2$H$_5$)$_3$::mixture of MgC$_2$H$_5$Br and Mg(C$_2$H$_5$)$_2$=1.0:3.7:1.0. The yield of the product is 750 g/g Ti(OC$_4$H$_9$)$_4$ or 5.3 kg/g Ti per hour. The product has the following composition (vol. %): 1-butene 96.9; 3-methyl-1-butene 1.1; 1-hexene 0 4; 2-ethyl-1-butene 1.6.

EXAMPLE 21

Dimerization of ethylene is carried out at 65° C. by following the procedure described in Example 16 but as MgRX use is made of MgC$_2$H$_5$Br. Mole ratio Ti-(OC$_4$H$_9$)$_4$: :Al(C$_2$H$_5$)$_3$:MgC$_2$H$_5$Br=1.0 3.7:1.0. The yield of the product is 872 g/g Ti(OC$_4$H$_9$)$_4$ per hour or 6.2 kg/g Ti per hour. The product has the following composition (vol. %): 1-butene 95.3; 3-methyl-1-butene 1.9; 1-hexene 0.3; 2-ethyl-1-butene 2.5.

EXAMPLE 22

Dimerization of ethylene is carried out at 25° C. under pressure 0.8 MPa by following the procedure described in Example 16 but as MgRX use is made of MgC$_4$H$_9$Cl. Mole ratio Ti(OC$_4$H$_9$)$_4$:Al(C$_2$H$_5$)$_3$:MgC$_4$H$_9$Cl==1.0:3.7:1.0. The yield o the product is 767 g/g Ti(OC$_4$H$_9$)$_4$ per hour or 5.4 kg/g Ti per hour. The product has the following composition (vol. %): 1-butene 96.2; 3-methyl-1-butene 1.1; 1-hexene 0.3; 2-ethyl-1-butene 2.4.

EXAMPLE 23 n-Heptane (200 ml) containing Ti(OC$_4$H$_9$)$_4$ (1.6×10$^{-3}$ mole), Al(C$_2$H$_5$)$_3$ (6.4×10$^{-23}$ mole) and MgC$_4$H$_9$Cl (6.4× 10$^{-23}$ mole) are fed into a reactor and then ethylene is delivered. Mole ratio Ti(OC$_4$H$_9$)$_4$:Al(C$_2$H$_5$)$_3$:MgC$_4$H$_9$Cl==1.0:4.0:4.0. The process is performed at 20° C. under ethylene pressure 1.0 MPa. The yield of the product is 1055 g/g Ti(OC$_4$N$_9$)$_4$ per hour or 7.8 kg/g Ti per hour. The product has the composition (vol. %): 1-butene 97.7; 3-methyl-1-pentene 0.8; 1-hexene 0.5; 2-ethyl-1-butene 1.0.

EXAMPLE 24

Dimerization of ethylene is carried out at 60° C. under ethylene pressure 3.0 MPa with the use of the catalyst described in Example 23. Diisopropyl ether is used as a solvent. Mole ratio Ti(OC$_4$H$_9$)$_4$:Al(C$_2$H$_5$)$_3$::MgC$_4$H$_9$Cl=1.0:5.0:1.0. The yield of the product is 910 g/g Ti(OC$_4$H$_9$)$_4$ per hour or 6.4 kg/g Ti per hour. The product has the following composition (vol. %): 1-butene 96.7; 3-methyl-1-pentene 1.4; 1-hexene 0.4; 2-ethyl-1-butene 1.5.

EXAMPLE 25

Dimerization of ethylene is carried out at 25° C. under ethylene pressure 1.0 MPa with the use of the catalyst described in Example 23. Mole ratio Ti-(OC$_4$H$_9$)$_4$: :Al(C$_2$H$_5$)$_3$:MgC$_4$N$_9$Cl=1.0:100:1.0. The yield of the product is 1020 g/g Ti(OC$_4$H$_9$)$_4$ per hour or 7.2 kg/g Ti per hour. The product has the following composition (vol. %): 1-butene 96.9; 3-methyl-1-pentene 1.5; 1-hexene 0.1; 2-ethyl-1-butene 1.5.

EXAMPLE 26

Dimerization of ethylene is carried out at 70° C. under ethylene pressure 2 MPa with the use of the catalyst described in Example 23.

As a solvent use is made of a mixture of 1-butene (60%) and hexenes (40%) as an Example 13. Mole ratio Ti(OC$_4$H$_9$)$_4$:Al(C$_2$H$_5$)$_3$:MgC$_4$H$_9$Cl=1.0:4.0:1.0. The yield of the product is 1300 g/g Ti(OC$_4$H$_9$) per hour or 9.2 kg/g Ti per hour. The product has the following composition (vol. %): 1-butene 97.0; 3-methyl-1-pentene 1.4; 1-hexene 0.1; 2-ethyl-1-butene 1.4; 1-octene 0.1.

EXAMPLE 27

Dimerization of ethylene is carried out at 65° C. under ethylene pressure 0.8 MPa with the use of the catalyst described in Example 23.

Diethyl ether is used as a solvent.

Mole ratio $Ti(OC_4H_9)_4:Al(C_2H_5)_3:MgC_4H_9Cl = 1.0:10:2.0$. The yield of the product is 750 g/g $Ti(OC_4H_9)_4$ per hour or 5.3 kg/g Ti per hour. The composition of the product (vol. %) is: 1-butene 96.0; 3-methyl-1-pentene 2.0; 1-hexene 0.3; 2-ethyl-1-butene 1.6.; 1-octene 0.1.

EXAMPLE 28

Ethylene dimerization is performed by following the procedure described in Example 27. Mole ratio $Ti(OC_4H_9)_4:Al(C_2H_5)_3:MgC_4H_9Cl = 1.0:25:2.0$. The yield of the product is 930 g/g $Ti(OC_4H_9)_4$ per hour or 6.6 kg/g Ti per hour. The product has the following composition (vol. %): 1-butene 98.7; 3-methyl-1-pentene 0.7; 2-ethyl-1-butene 0.4; 1-octene 0.2.

EXAMPLE 29

Dimerization is performed at 0° C. under ethylene pressure 1.5 MPa as described in Example 23. The yield of the product is 504 g/g $Ti(OC_4H_9)_4$ per hour or 3.6 kg/g Ti per hour. The product has the following composition (vol. %): 1-butene 94.6; 3-methyl-1-pentene 3.1; 2-ethyl-1-butene 1.7; 1-hexene 0.6; polymer traces.

INDUSTRIAL APPLICABILITY

The proposed method can find application in production of raw material for synthesis of plastic materials, divinyl, isoprene, or additives to motor fuels.

We claim:

1. A method of preparing 1-butene and/or hexenes comprising dimerizing ethylene in the presence of a complex organo metallic catalyst containing titanium alcoholate of the formula $Ti(OR^1)_4$, where $R^1$ is an alkyl radical having from 1 to 8 carbon atoms or aryl, trialkylaluminium of the formula $AlR^2_3$, where $R^2$ is an alkyl radical having from 1 to 6 carbon atoms and an organomagnesium compound of the formula $MgR^3_2$ and/or $MgR^3X$, where $R^3$ is an alkyl radical having from 1 to 4 carbon atoms and X is Br, Cl or I at a temperature of from 0° to 100° C. under pressure from 0.1 to 4 mps in an organic solvent.

2. A method as claimed in claim 1 wherein the complex organometallic catalyst contains $Ti(OR^1)_4$, $AlR^2_3$, $MgR^3_2$ and/or $MgR^3X$ at a mole ratio of 1.0:1.0–100:0.2–5.0, respectively.

3. A method as claimed in claim 1 or 2, wherein the hydrocarbon organic solvent is 1-butene and/or hexene fraction.

* * * * *